(12) United States Patent
Levine et al.

(10) Patent No.: US 8,764,779 B2
(45) Date of Patent: *Jul. 1, 2014

(54) ROTATIONAL THROMBECTOMY WIRE

(75) Inventors: Marc-Alan Levine, Pottstown, PA (US); Michael Leedle, Conshohocken, PA (US)

(73) Assignee: Rex Medical, L.P., Conshohocken, PA (US)

( * ) Notice: Subject to any disclaimer, the term of this patent is extended or adjusted under 35 U.S.C. 154(b) by 31 days.

This patent is subject to a terminal disclaimer.

(21) Appl. No.: 13/303,339

(22) Filed: Nov. 23, 2011

(65) Prior Publication Data

US 2012/0116429 A1 May 10, 2012

Related U.S. Application Data

(63) Continuation-in-part of application No. 13/095,329, filed on Apr. 27, 2011.

(60) Provisional application No. 61/431,169, filed on Jan. 10, 2011, provisional application No. 61/334,412, filed on May 13, 2010.

(51) Int. Cl.
*A61B 17/22* (2006.01)

(52) U.S. Cl.
USPC .......................................................... 606/159

(58) Field of Classification Search
USPC .......... 606/110–115, 127, 128, 159, 170, 180
See application file for complete search history.

(56) References Cited

U.S. PATENT DOCUMENTS

| | | |
|---|---|---|
| 3,612,058 A | 10/1971 | Ackerman |
| 3,749,085 A | 7/1973 | Willson et al. |
| 4,038,985 A | 8/1977 | Chiulli |
| 4,579,127 A | 4/1986 | Haacke |
| 4,745,919 A | 5/1988 | Bundy |
| 4,765,332 A | 8/1988 | Fischell et al. |
| 4,784,636 A | 11/1988 | Rydell |
| 4,842,579 A | 6/1989 | Shiber |
| 4,883,460 A | 11/1989 | Zanetti |
| 4,895,560 A | 1/1990 | Papantonakos |
| 4,906,244 A | 3/1990 | Pinchuk et al. |
| 4,950,277 A | 8/1990 | Farr |
| 4,979,951 A | 12/1990 | Simpson |
| 4,984,581 A | 1/1991 | Stice et al. |
| 4,990,134 A | 2/1991 | Auth |
| 5,009,659 A | 4/1991 | Hamlin et al. |

(Continued)

FOREIGN PATENT DOCUMENTS

| | | |
|---|---|---|
| DE | 1075903 | 2/1960 |
| DE | 3804849 | 9/1988 |

(Continued)

*Primary Examiner* — Ryan Severson
(74) *Attorney, Agent, or Firm* — Neil D. Gershon

(57) ABSTRACT

A rotational thrombectomy wire for breaking up vascular thrombus or other obstructive material having a core having a proximal region and a distal region and being rotatable by a motor. The distal region has a smaller diameter than the proximal region. A cable is coupled to the distal region of the core and extends distally thereof. A torque tube is positioned over the cable and a coil is positioned over a distal portion of the cable. A distal portion of the cable has a non-linear configuration. A first covering material is positioned over the coil.

11 Claims, 12 Drawing Sheets

(56) References Cited

U.S. PATENT DOCUMENTS

| | | | |
|---|---|---|---|
| 5,025,799 A | 6/1991 | Wilson | |
| 5,026,384 A | 6/1991 | Farr et al. | |
| 5,030,201 A | 7/1991 | Palestrant | |
| 5,041,082 A | 8/1991 | Shiber | |
| 5,067,489 A | 11/1991 | Lind et al. | |
| 5,067,957 A | 11/1991 | Jervis | |
| 5,097,849 A | 3/1992 | Kensey | |
| 5,131,406 A | 7/1992 | Kaltenback | |
| 5,192,268 A | 3/1993 | Shiber | |
| 5,192,290 A | 3/1993 | Hilal | |
| 5,203,772 A | 4/1993 | Hammerslag et al. | |
| 5,211,183 A | 5/1993 | Wilson | |
| 5,213,111 A | 5/1993 | Cook | |
| 5,217,026 A | 6/1993 | Stoy | |
| 5,251,640 A | 10/1993 | Osborne | |
| 5,253,653 A | 10/1993 | Daigle | |
| 5,261,877 A | 11/1993 | Fine et al. | |
| 5,273,526 A | 12/1993 | Dance | |
| 5,299,580 A | 4/1994 | Atkinson | |
| 5,313,967 A | 5/1994 | Lieber | |
| 5,314,407 A | 5/1994 | Auth et al. | |
| 5,314,438 A | 5/1994 | Shturman | |
| 5,333,620 A | 8/1994 | Moutafis et al. | |
| 5,341,818 A | 8/1994 | Abrams | |
| 5,345,945 A | 9/1994 | Hodgson | |
| 5,356,418 A | 10/1994 | Shturman | |
| 5,372,144 A | 12/1994 | Martier | |
| 5,376,100 A | 12/1994 | Lefebvre | |
| 5,383,460 A | 1/1995 | Jang et al. | |
| 5,395,311 A | 3/1995 | Andrews | |
| 5,395,384 A | 3/1995 | Duthoit | |
| 5,429,136 A | 7/1995 | Milo et al. | |
| 5,431,673 A | 7/1995 | Summers et al. | |
| 5,452,726 A | 9/1995 | Burmeister | |
| 5,490,859 A | 2/1996 | Mische | |
| 5,501,694 A | 3/1996 | Ressemann et al. | |
| 5,514,128 A | 5/1996 | Hillsman | |
| 5,529,580 A | 6/1996 | Kusunoki et al. | |
| 5,536,242 A | 7/1996 | Willard et al. | |
| 5,540,707 A * | 7/1996 | Ressemann et al. | 606/159 |
| 5,551,443 A | 9/1996 | Sepetka | |
| 5,556,408 A | 9/1996 | Farhat | |
| 5,562,275 A | 10/1996 | Weissenfluh | |
| 5,569,179 A | 10/1996 | Adrian et al. | |
| 5,569,275 A | 10/1996 | Kotula et al. | |
| 5,584,843 A | 12/1996 | Wulfman | |
| 5,605,162 A | 2/1997 | Mirzaee | |
| 5,609,602 A | 3/1997 | Machemer et al. | |
| 5,611,807 A | 3/1997 | O'Boyle | |
| 5,634,897 A | 6/1997 | Dance | |
| 5,653,722 A | 8/1997 | Kieturakis | |
| 5,695,506 A | 12/1997 | Pike et al. | |
| 5,712,543 A | 1/1998 | Sjostrom | |
| 5,746,701 A | 5/1998 | Noone | |
| 5,749,885 A | 5/1998 | Sjostrom et al. | |
| 5,762,637 A | 6/1998 | Berg et al. | |
| 5,766,191 A | 6/1998 | Trerotola | |
| 5,797,856 A | 8/1998 | Frisbie et al. | |
| 5,833,631 A | 11/1998 | Nguyen | |
| 5,836,868 A | 11/1998 | Ressemann et al. | |
| 5,836,893 A | 11/1998 | Urick | |
| 5,840,046 A | 11/1998 | Deem | |
| 5,843,103 A | 12/1998 | Wulfman | |
| 5,879,361 A | 3/1999 | Nash | |
| 5,885,227 A | 3/1999 | Finlayson | |
| 5,895,399 A | 4/1999 | Barbut | |
| 5,897,567 A | 4/1999 | Ressemann et al. | |
| 5,902,263 A | 5/1999 | Patterson | |
| 5,902,268 A | 5/1999 | Saab | |
| 5,906,627 A | 5/1999 | Spaulding | |
| 5,910,364 A | 6/1999 | Miyata | |
| 5,916,166 A | 6/1999 | Reiss | |
| 5,924,998 A | 7/1999 | Cornelius | |
| 5,938,623 A | 8/1999 | Quiachon | |
| 5,938,645 A | 8/1999 | Gordon | |
| 5,957,941 A | 9/1999 | Ream | |
| 5,971,991 A | 10/1999 | Sunderland | |
| 5,984,877 A | 11/1999 | Fleischhacker, Jr. | |
| 6,004,279 A | 12/1999 | Crowley | |
| 6,007,533 A | 12/1999 | Casscells et al. | |
| 6,019,736 A | 2/2000 | Avellanet | |
| 6,022,363 A | 2/2000 | Walker | |
| 6,024,749 A | 2/2000 | Shturman et al. | |
| 6,059,745 A | 5/2000 | Gelbfish | |
| 6,077,282 A | 6/2000 | Shturman et al. | |
| 6,080,117 A | 6/2000 | Cornelius | |
| 6,080,170 A | 6/2000 | Nash et al. | |
| 6,083,198 A | 7/2000 | Afzal | |
| 6,090,118 A | 7/2000 | McGuckin, Jr. | |
| 6,090,123 A | 7/2000 | Culp et al. | |
| 6,096,001 A | 8/2000 | Drasler et al. | |
| 6,106,485 A | 8/2000 | McMahan | |
| 6,113,614 A | 9/2000 | Mears | |
| 6,120,515 A | 9/2000 | Rogers et al. | |
| 6,126,635 A | 10/2000 | Simpson | |
| 6,143,009 A | 11/2000 | Shiber | |
| 6,165,140 A | 12/2000 | Ferrera et al. | |
| 6,168,570 B1 | 1/2001 | Ferrera et al. | |
| 6,185,449 B1 | 2/2001 | Berg | |
| 6,206,898 B1 | 3/2001 | Honeycutt et al. | |
| 6,217,589 B1 | 4/2001 | McAlister | |
| 6,217,595 B1 | 4/2001 | Shturman | |
| 6,251,085 B1 | 6/2001 | Tezuka | |
| 6,251,086 B1 | 6/2001 | Cornelius | |
| 6,251,121 B1 | 6/2001 | Saadat | |
| 6,254,550 B1 | 7/2001 | McNamara | |
| 6,309,399 B1 | 10/2001 | Barbut et al. | |
| 6,319,242 B1 | 11/2001 | Patterson et al. | |
| 6,319,262 B1 * | 11/2001 | Bates et al. | 606/127 |
| 6,322,572 B1 | 11/2001 | Lee | |
| 6,328,752 B1 | 12/2001 | Sjostrom et al. | |
| 6,371,928 B1 | 4/2002 | Mcfann | |
| 6,398,773 B1 | 6/2002 | Bagaoisan et al. | |
| 6,413,222 B1 | 7/2002 | Pantages et al. | |
| 6,432,066 B1 | 8/2002 | Ferrera et al. | |
| 6,451,036 B1 | 9/2002 | Heitzmann et al. | |
| 6,454,717 B1 | 9/2002 | Pantages et al. | |
| 6,454,779 B1 | 9/2002 | Taylor | |
| 6,458,127 B1 | 10/2002 | Truckai et al. | |
| 6,475,222 B1 | 11/2002 | Berg et al. | |
| 6,475,224 B1 | 11/2002 | Pantages et al. | |
| 6,475,226 B1 | 11/2002 | Belef | |
| 6,482,215 B1 | 11/2002 | Shiber | |
| 6,482,217 B1 | 11/2002 | Pintor et al. | |
| 6,485,482 B1 | 11/2002 | Belef | |
| 6,491,660 B2 | 12/2002 | Guo et al. | |
| 6,494,890 B1 | 12/2002 | Shturman | |
| 6,508,782 B1 | 1/2003 | Evans | |
| 6,508,825 B1 | 1/2003 | Selmon et al. | |
| 6,517,528 B1 | 2/2003 | Pantages et al. | |
| 6,517,560 B1 | 2/2003 | Toth et al. | |
| 6,565,588 B1 | 5/2003 | Clement et al. | |
| 6,569,147 B1 | 5/2003 | Evans et al. | |
| 6,572,630 B1 | 6/2003 | McGuckin | |
| 6,579,246 B2 | 6/2003 | Jacobson | |
| 6,579,299 B2 | 6/2003 | McGuckin | |
| 6,602,207 B1 | 8/2003 | Mam | |
| 6,602,262 B2 * | 8/2003 | Griego et al. | 606/113 |
| 6,602,264 B1 | 8/2003 | McGuckin | |
| 6,620,114 B2 | 9/2003 | Vrba et al. | |
| 6,620,179 B2 | 9/2003 | Boock | |
| 6,632,230 B2 | 10/2003 | Barry | |
| 6,648,337 B1 | 11/2003 | Baehl | |
| 6,652,480 B1 | 11/2003 | Imran et al. | |
| 6,652,546 B1 | 11/2003 | Nash | |
| 6,660,014 B2 | 12/2003 | Demarais | |
| 6,663,613 B1 | 12/2003 | Evans et al. | |
| 6,666,874 B2 | 12/2003 | Heitzmann et al. | |
| 6,669,652 B2 | 12/2003 | Anderson | |
| 6,673,025 B1 | 1/2004 | Richardson | |
| 6,685,718 B1 | 2/2004 | Wyzgala et al. | |
| 6,689,089 B1 | 2/2004 | Tiedtke et al. | |
| 6,702,830 B1 | 3/2004 | Demarais et al. | |
| 6,719,717 B1 | 4/2004 | Johnson et al. | |

(56) References Cited

U.S. PATENT DOCUMENTS

| | | | |
|---|---|---|---|
| 6,746,462 B1 | 6/2004 | Selmon et al. | |
| 6,767,353 B1 | 7/2004 | Shiber | |
| 6,790,215 B2 | 9/2004 | Findlay | |
| 6,805,676 B2 | 10/2004 | Klint | |
| 6,805,684 B2 | 10/2004 | Bonnette et al. | |
| 6,818,001 B2 | 11/2004 | Wulfman et al. | |
| 6,824,545 B2 * | 11/2004 | Sepetka et al. | 606/113 |
| 6,830,577 B2 | 12/2004 | Nash et al. | |
| 6,881,194 B2 | 4/2005 | Miyata et al. | |
| 6,911,016 B2 | 6/2005 | Balzum et al. | |
| 6,926,725 B2 | 8/2005 | Cooke et al. | |
| 6,929,633 B2 | 8/2005 | Evans et al. | |
| 7,037,316 B2 | 5/2006 | McGuckin, Jr. et al. | |
| 7,074,197 B2 | 7/2006 | Reynolds et al. | |
| 7,115,101 B2 | 10/2006 | Cornelius et al. | |
| 7,150,756 B2 | 12/2006 | Levinson et al. | |
| 7,169,118 B2 | 1/2007 | Reynolds | |
| 7,172,610 B2 | 2/2007 | Heitzmann et al. | |
| 7,179,269 B2 | 2/2007 | Welch et al. | |
| 7,220,269 B1 | 5/2007 | Ansel et al. | |
| 7,309,318 B2 | 12/2007 | Cassell et al. | |
| 7,399,307 B2 | 7/2008 | Evans et al. | |
| 7,407,506 B2 | 8/2008 | Makower | |
| 7,434,437 B2 | 10/2008 | Kato | |
| 7,462,187 B2 | 12/2008 | Johnston et al. | |
| 7,470,239 B1 | 12/2008 | Rooney et al. | |
| 7,473,263 B2 | 1/2009 | Johnston et al. | |
| 7,488,322 B2 | 2/2009 | Brunnett | |
| 7,494,468 B2 | 2/2009 | Rabiner et al. | |
| 7,494,687 B2 | 2/2009 | Cox | |
| 7,507,246 B2 * | 3/2009 | McGuckin et al. | 606/159 |
| 7,517,351 B2 | 4/2009 | Culp et al. | |
| 7,575,585 B2 | 8/2009 | Goto et al. | |
| 7,621,880 B2 | 11/2009 | Ryan et al. | |
| 7,628,763 B2 | 12/2009 | Noriega et al. | |
| 7,645,242 B1 | 1/2010 | Jalisi et al. | |
| 7,645,261 B2 | 1/2010 | Hinchliffe | |
| 7,655,016 B2 | 2/2010 | Demarais et al. | |
| 7,744,545 B2 | 6/2010 | Aimi et al. | |
| 7,762,962 B2 | 7/2010 | Mishima | |
| 7,763,010 B2 | 7/2010 | Evans et al. | |
| 7,776,062 B2 | 8/2010 | Besselink et al. | |
| 7,780,650 B2 | 8/2010 | Frassica et al. | |
| 7,794,414 B2 | 9/2010 | Rabiner et al. | |
| 7,819,887 B2 | 10/2010 | McGuckin, et al. | |
| 7,824,345 B2 | 11/2010 | Euteneuer et al. | |
| 7,862,575 B2 | 1/2011 | Tal | |
| 7,878,935 B2 | 2/2011 | Lahr | |
| 7,878,985 B2 | 2/2011 | Cornish et al. | |
| 7,883,474 B1 | 2/2011 | Mirigian et al. | |
| 8,062,317 B2 | 11/2011 | McGuckin et al. | |
| 8,246,641 B2 * | 8/2012 | Osborne et al. | 606/159 |
| 2001/0009980 A1 | 7/2001 | Richardson et al. | |
| 2001/0031981 A1 | 10/2001 | Evans | |
| 2002/0013548 A1 | 1/2002 | Hinchliffe | |
| 2002/0058956 A1 | 5/2002 | Honeycutt et al. | |
| 2002/0095102 A1 | 7/2002 | Winters | |
| 2002/0143350 A1 | 10/2002 | Heitzmann et al. | |
| 2002/0165567 A1 | 11/2002 | Shiber | |
| 2002/0173812 A1 | 11/2002 | McGuckin, Jr. | |
| 2003/0023190 A1 | 1/2003 | Cox | |
| 2003/0139750 A1 | 7/2003 | Shinozuka et al. | |
| 2003/0181828 A1 | 9/2003 | Fujimoto | |
| 2003/0191483 A1 | 10/2003 | Cooke et al. | |
| 2003/0216668 A1 | 11/2003 | Howland | |
| 2004/0030266 A1 | 2/2004 | Murayama | |
| 2004/0073243 A1 | 4/2004 | Sepetka et al. | |
| 2004/0167436 A1 | 8/2004 | Reynolds | |
| 2004/0167442 A1 | 8/2004 | Shireman | |
| 2004/0167443 A1 | 8/2004 | Shireman | |
| 2004/0181175 A1 | 9/2004 | Clayman | |
| 2004/0193073 A1 | 9/2004 | DeMello | |
| 2005/0004517 A1 | 1/2005 | Courtney et al. | |
| 2005/0054951 A1 | 3/2005 | Parins | |
| 2005/0055040 A1 | 3/2005 | Tal | |
| 2005/0137501 A1 | 6/2005 | Euteneuer et al. | |
| 2005/0240146 A1 | 10/2005 | Nash et al. | |
| 2006/0074441 A1 | 4/2006 | McGuckin, Jr. et al. | |
| 2006/0106407 A1 | 5/2006 | McGuckin, Jr. et al. | |
| 2006/0142793 A9 | 6/2006 | Prudnikov et al. | |
| 2006/0276814 A1 | 12/2006 | Omata et al. | |
| 2007/0060911 A1 | 3/2007 | Webster et al. | |
| 2007/0088323 A1 | 4/2007 | Campbell et al. | |
| 2007/0161963 A1 | 7/2007 | Smalling | |
| 2007/0219484 A1 | 9/2007 | Straub | |
| 2007/0239182 A1 | 10/2007 | Glines et al. | |
| 2007/0250096 A1 | 10/2007 | Yamane et al. | |
| 2007/0282359 A1 | 12/2007 | Tal | |
| 2007/0282539 A1 | 12/2007 | Metcalf | |
| 2008/0091223 A1 | 4/2008 | Pokorney et al. | |
| 2008/0103516 A1 | 5/2008 | Wulfman et al. | |
| 2008/0188793 A1 | 8/2008 | Kozak et al. | |
| 2008/0208233 A1 | 8/2008 | Barnes et al. | |
| 2008/0228208 A1 | 9/2008 | Wulfman et al. | |
| 2008/0300532 A1 | 12/2008 | Bonnette et al. | |
| 2008/0319462 A1 | 12/2008 | Montague et al. | |
| 2009/0018567 A1 | 1/2009 | Escudero et al. | |
| 2009/0048537 A1 | 2/2009 | Lydon et al. | |
| 2009/0062773 A1 | 3/2009 | Cornish | |
| 2009/0112127 A1 | 4/2009 | Keating et al. | |
| 2009/0138031 A1 | 5/2009 | Tsukernik | |
| 2009/0143702 A1 | 6/2009 | Fleischhacker | |
| 2009/0209987 A1 | 8/2009 | Mathews et al. | |
| 2009/0227900 A1 | 9/2009 | Kim et al. | |
| 2009/0234378 A1 | 9/2009 | Escudero et al. | |
| 2009/0270791 A1 | 10/2009 | Todd | |
| 2009/0306546 A1 | 12/2009 | Knapp | |
| 2009/0318835 A1 | 12/2009 | Ressemann et al. | |
| 2010/0004561 A1 | 1/2010 | Nabeshima | |
| 2010/0004562 A1 | 1/2010 | Jalisi et al. | |
| 2010/0049225 A1 | 2/2010 | To et al. | |
| 2010/0069794 A1 | 3/2010 | Uihlein | |
| 2010/0094201 A1 | 4/2010 | Mallaby | |
| 2010/0168619 A1 | 7/2010 | Elsesser | |
| 2010/0211087 A1 * | 8/2010 | Osborne | 606/159 |
| 2010/0222786 A1 | 9/2010 | Kassab | |
| 2010/0249655 A1 | 9/2010 | Lemon | |
| 2010/0305592 A1 * | 12/2010 | McGuckin et al. | 606/159 |
| 2010/0312263 A1 | 12/2010 | Moberg et al. | |
| 2011/0004107 A1 | 1/2011 | Rosenthal et al. | |
| 2011/0077673 A1 | 3/2011 | Grubac et al. | |
| 2011/0077674 A1 | 3/2011 | Sullivan et al. | |
| 2011/0087254 A1 | 4/2011 | Welty | |
| 2011/0112563 A1 | 5/2011 | To et al. | |
| 2011/0125176 A1 | 5/2011 | Yates et al. | |
| 2011/0230862 A1 | 9/2011 | Segner et al. | |
| 2011/0282370 A1 | 11/2011 | Levine et al. | |
| 2012/0035634 A1 * | 2/2012 | McGuckin et al. | 606/159 |
| 2012/0116429 A1 * | 5/2012 | Levine et al. | 606/159 |
| 2012/0239066 A1 * | 9/2012 | Levine et al. | 606/159 |

FOREIGN PATENT DOCUMENTS

| | | |
|---|---|---|
| DE | WO 00/32265 | 6/2000 |
| DE | WO 2009/029430 | 3/2009 |
| EP | 0358825 | 9/1988 |
| EP | 0409372 | 2/1990 |
| JP | 56020839 | 2/1981 |
| JP | 03-186256 | 8/1991 |
| JP | 06-197899 | 7/1994 |
| WO | WO-9505209 | 2/1995 |
| WO | WO-98/38926 | 9/1998 |
| WO | WO-9923958 | 5/1999 |
| WO | WO-99/56638 | 11/1999 |

* cited by examiner

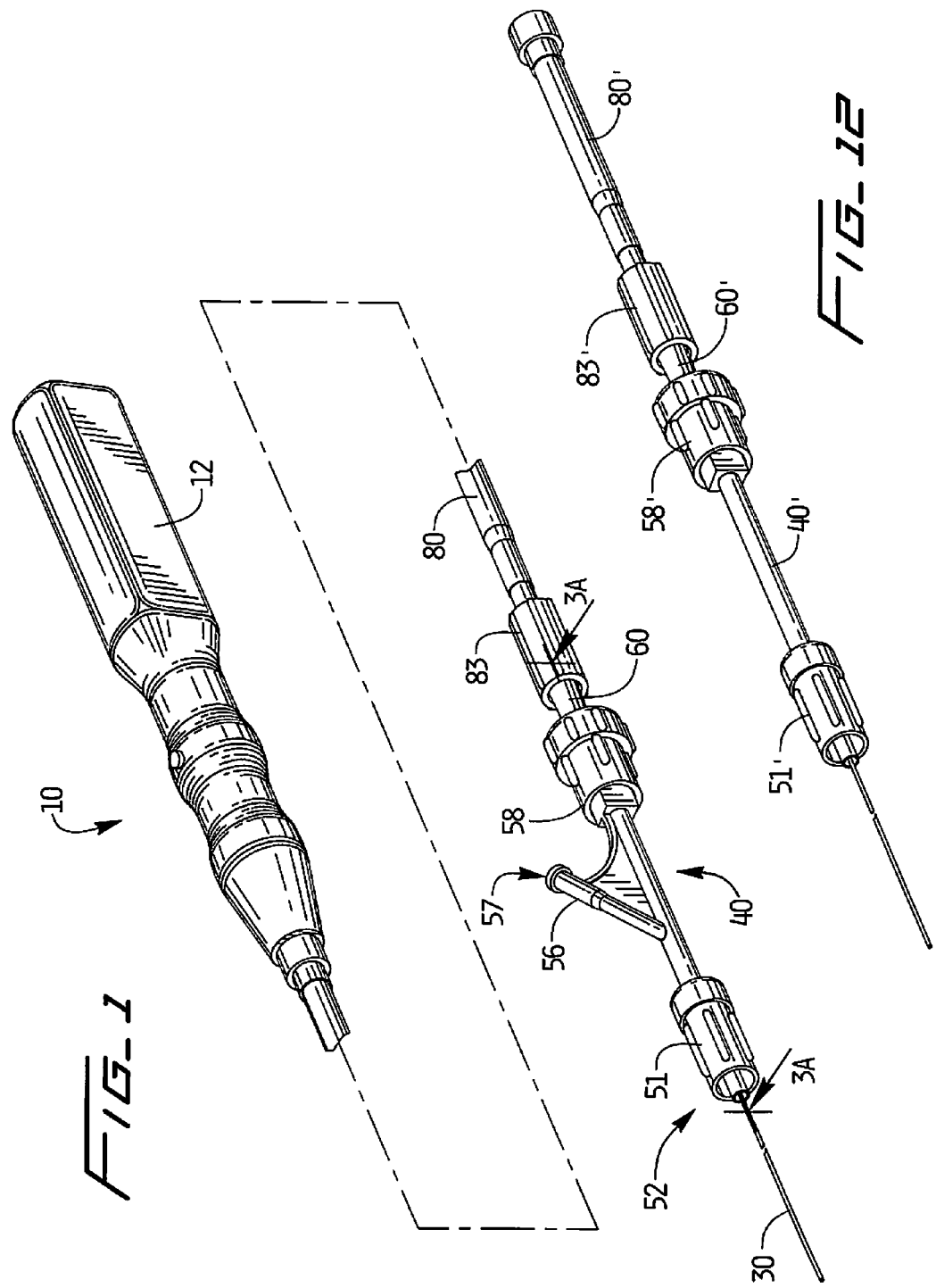

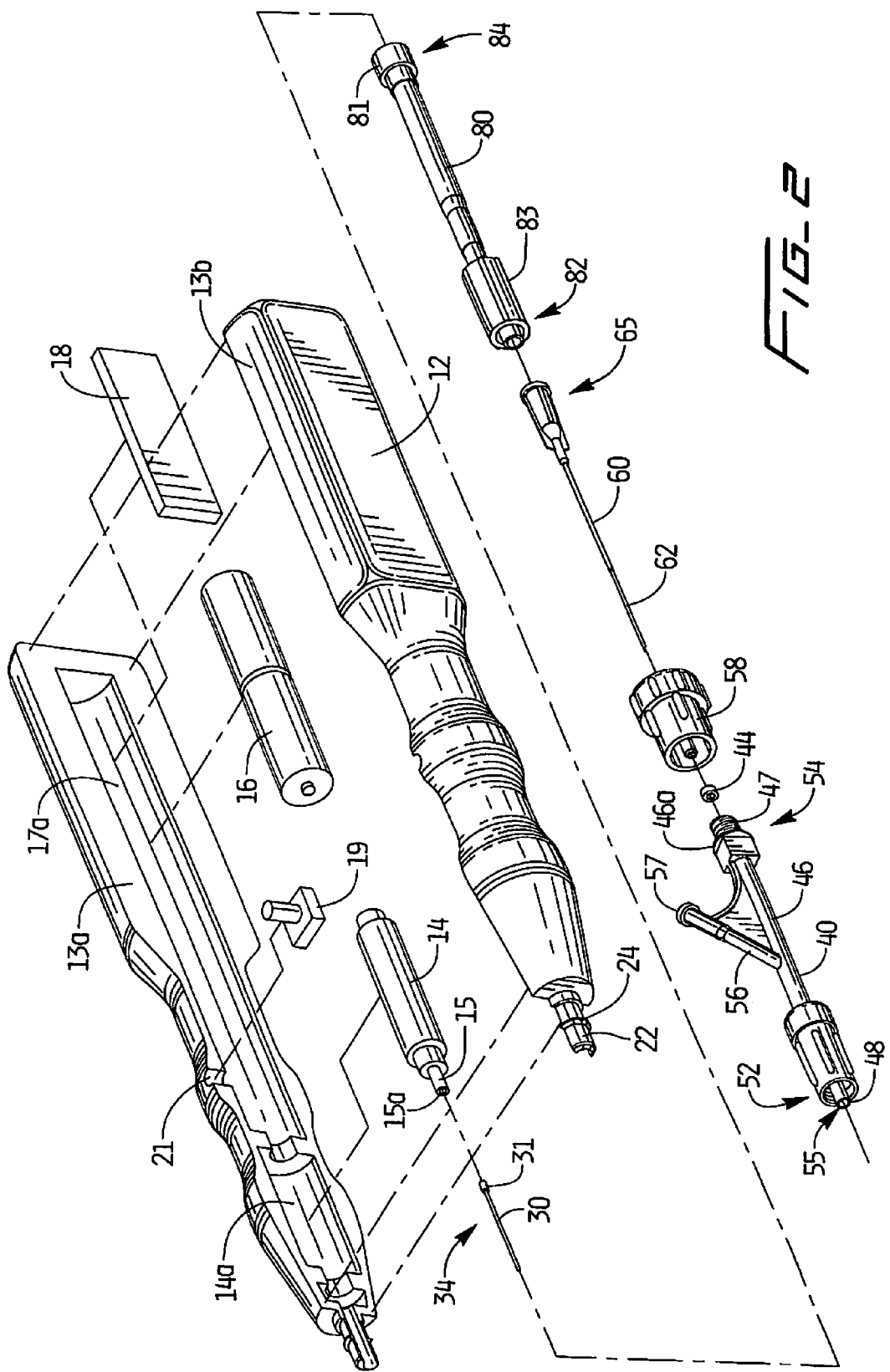

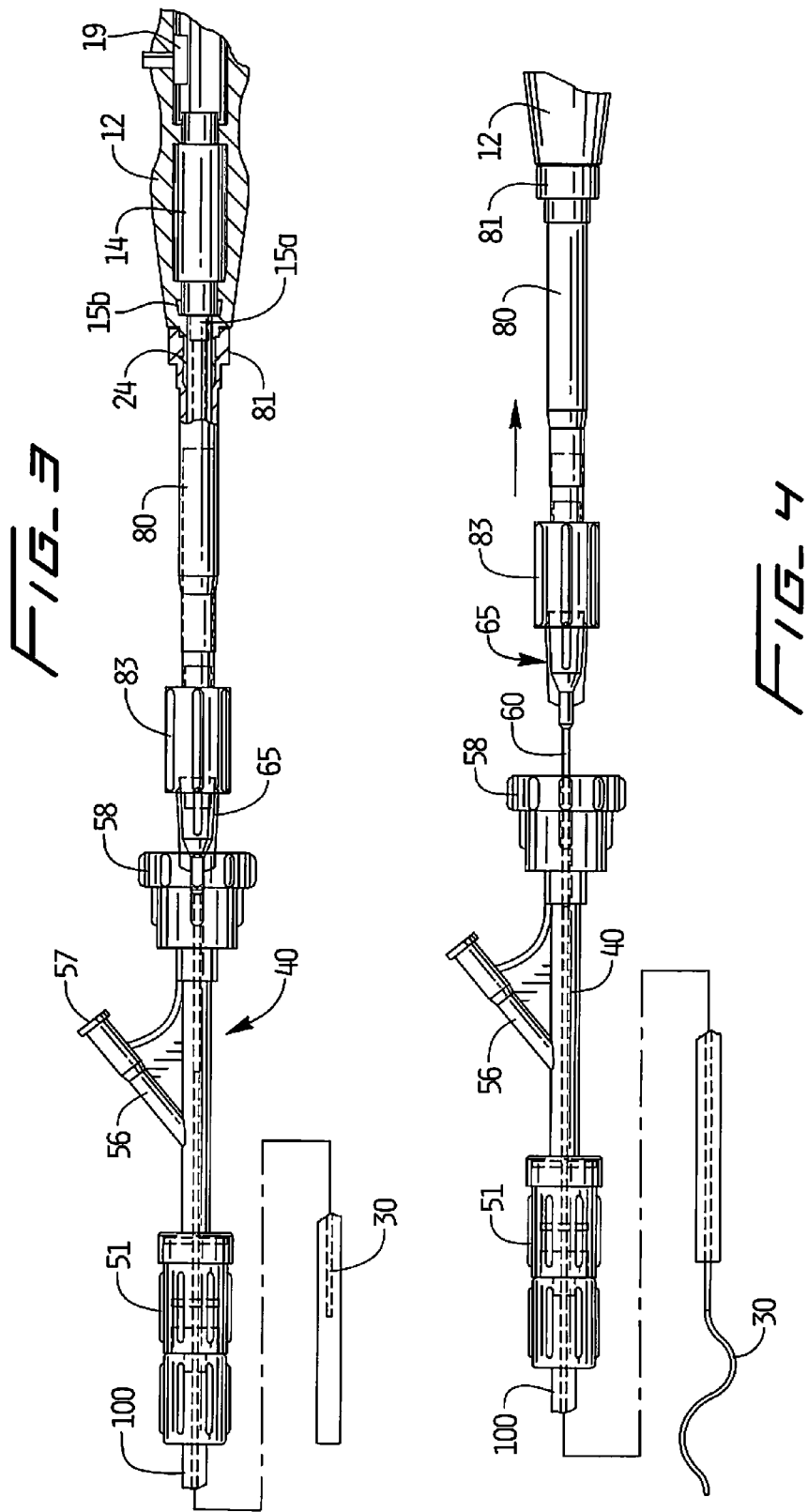

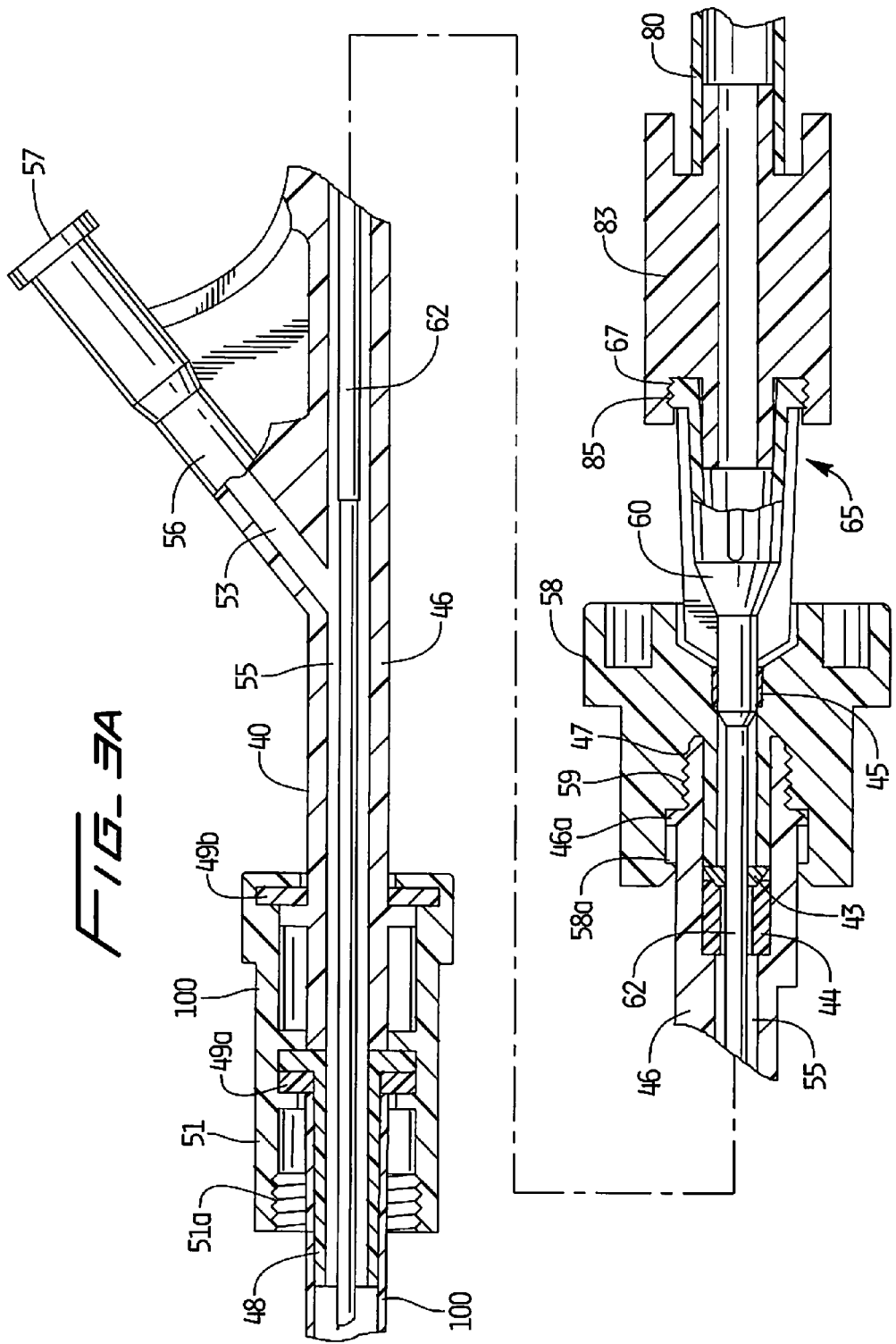

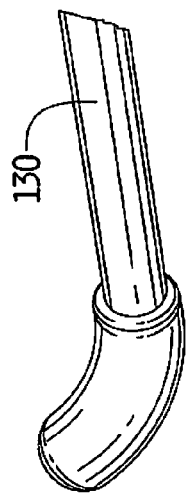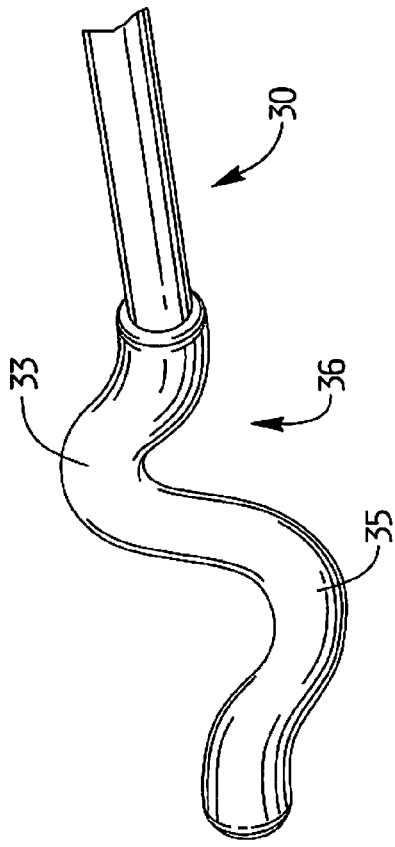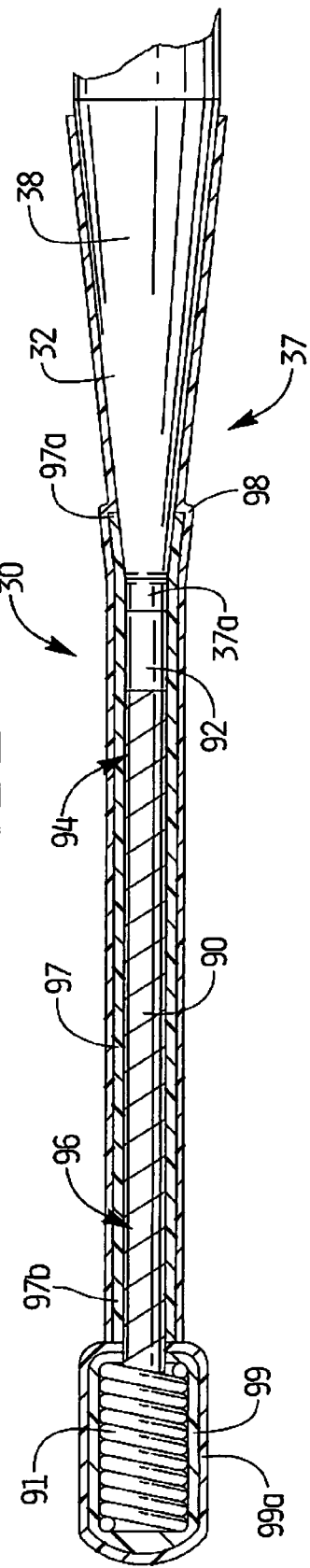

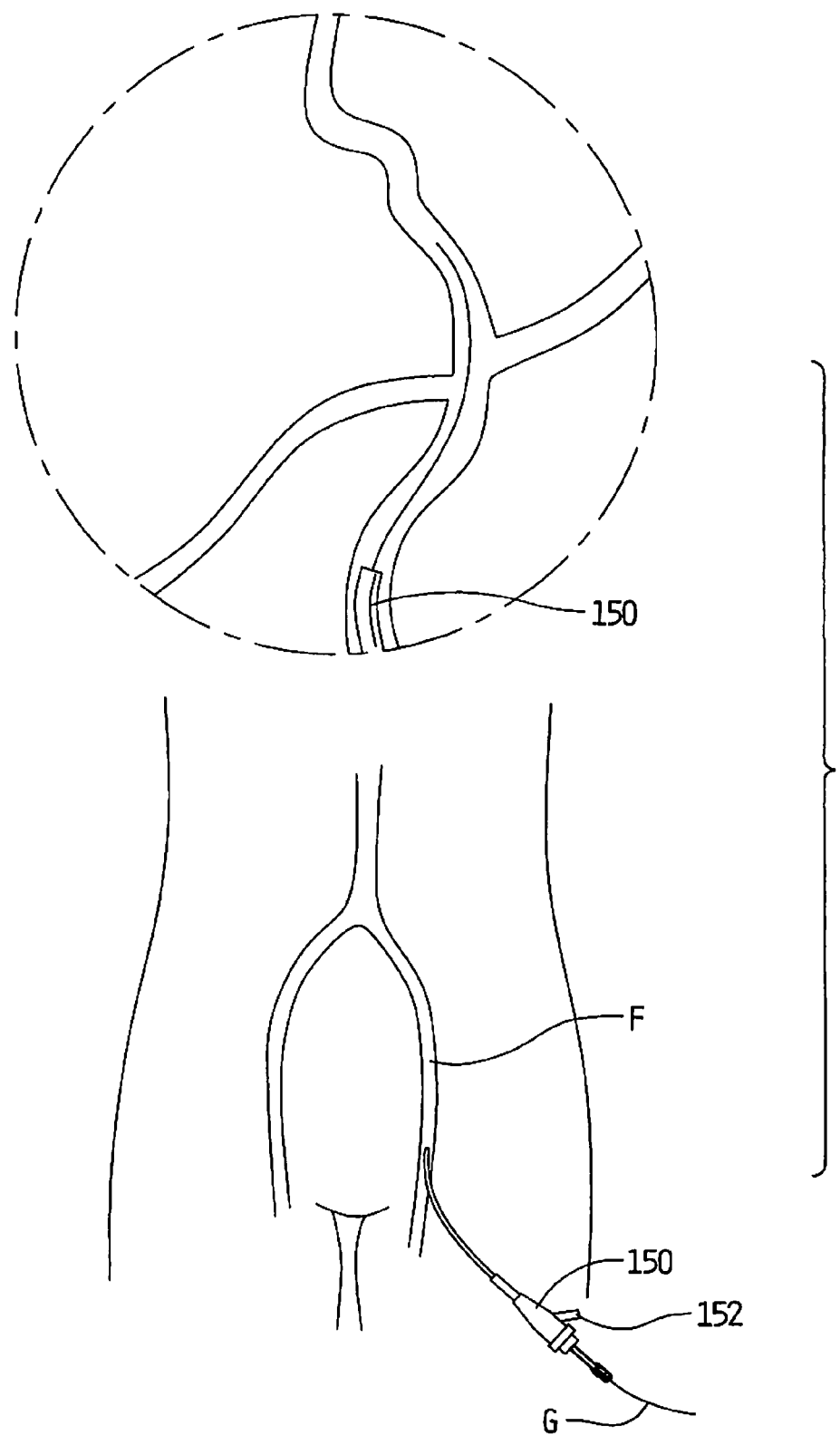
FIG_8

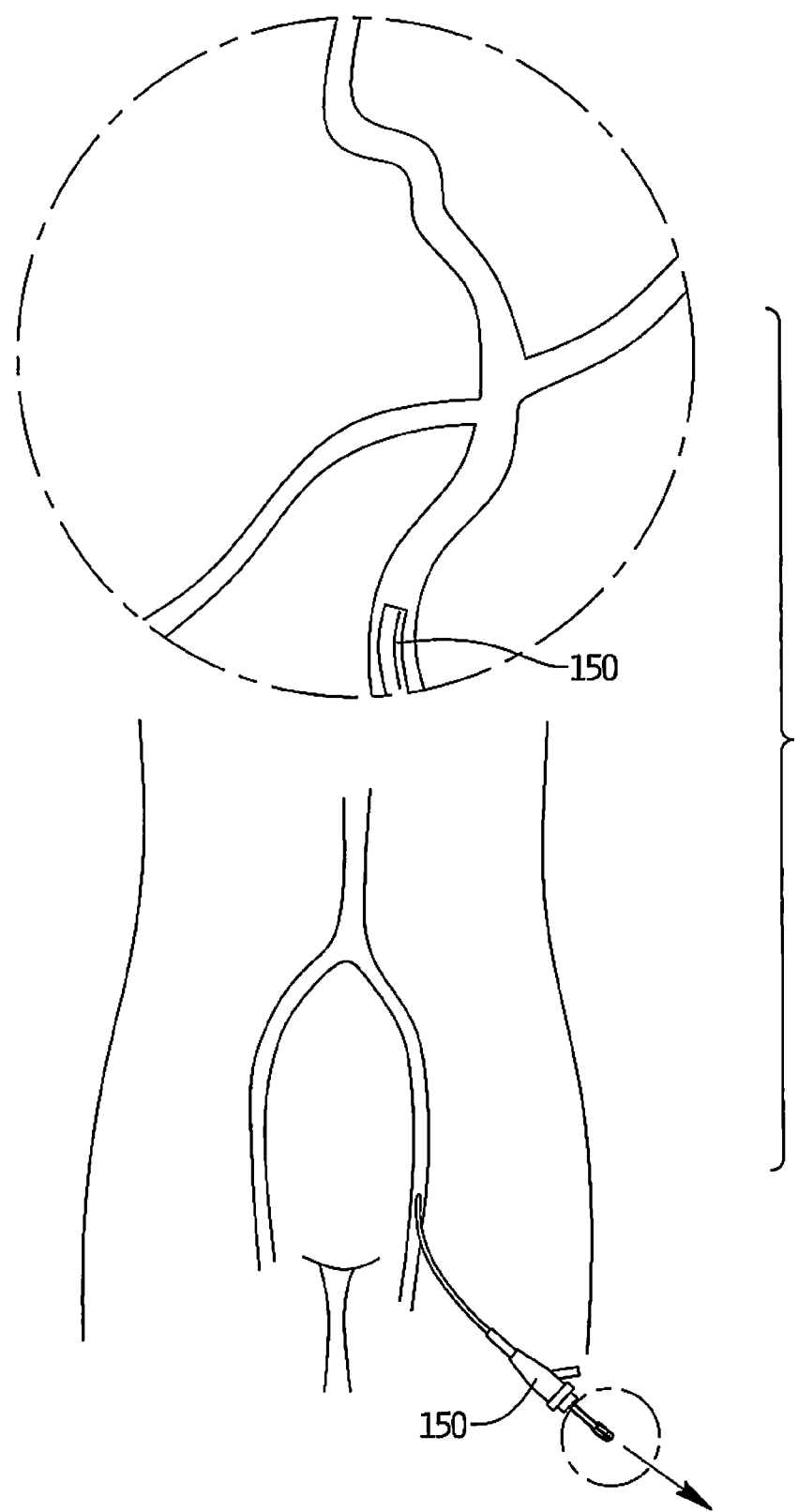
FIG_9

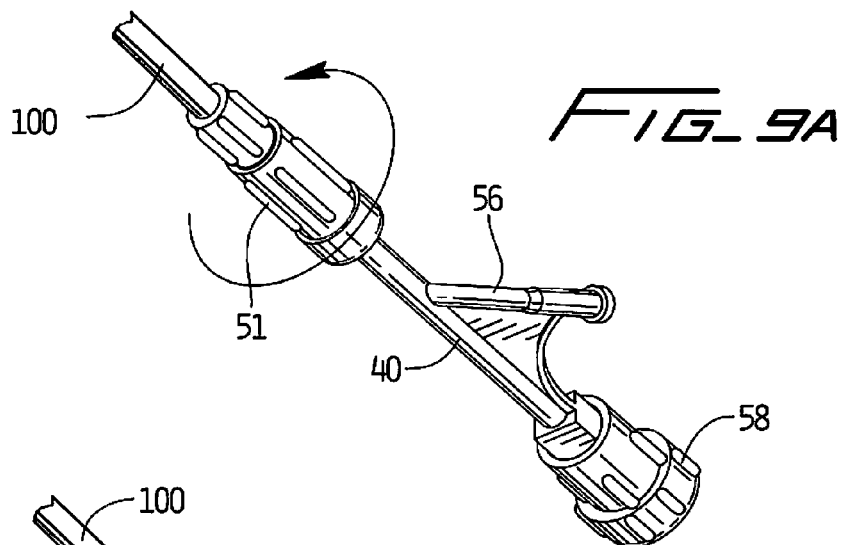
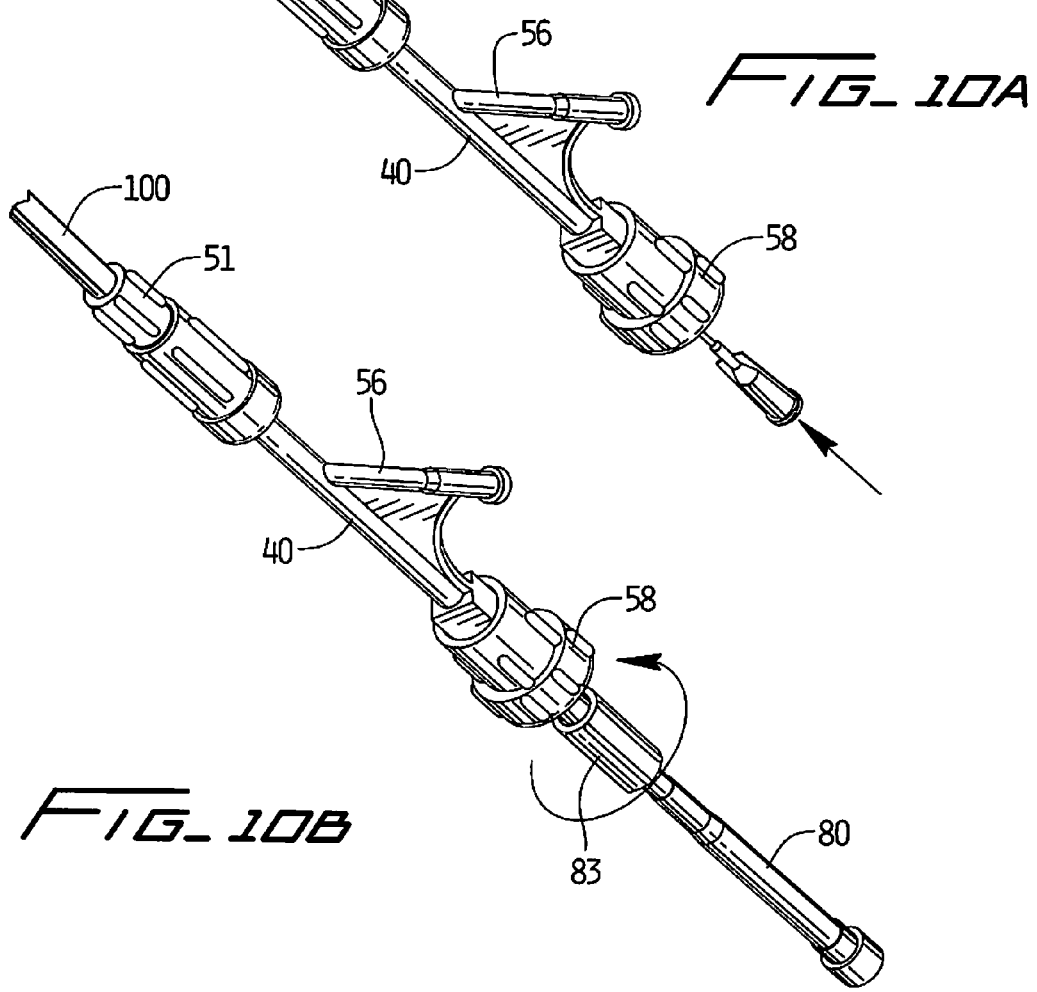

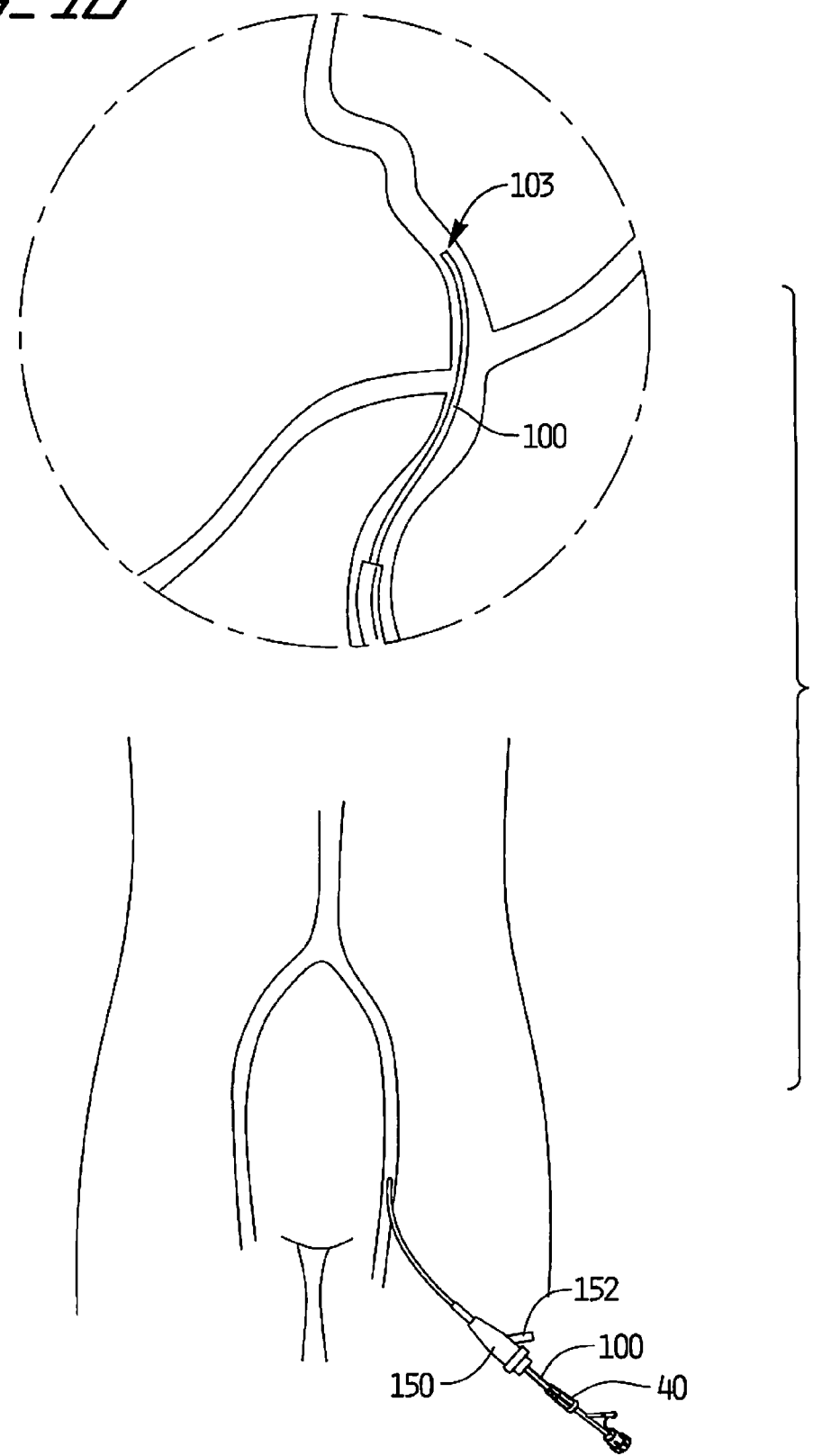
FIG_10

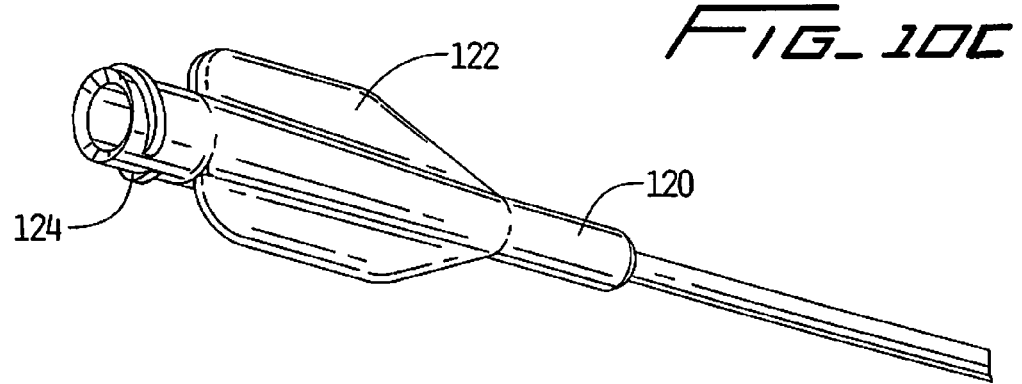
FIG_10C
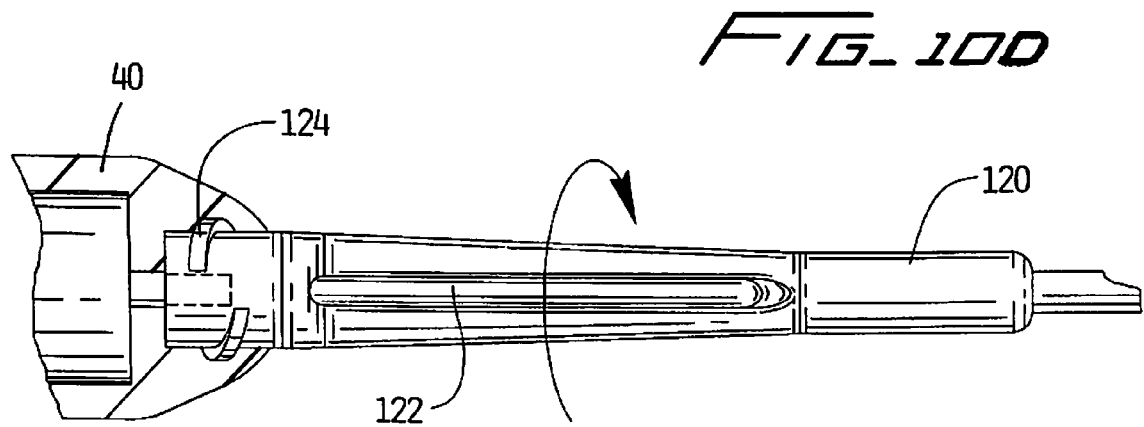
FIG_10D

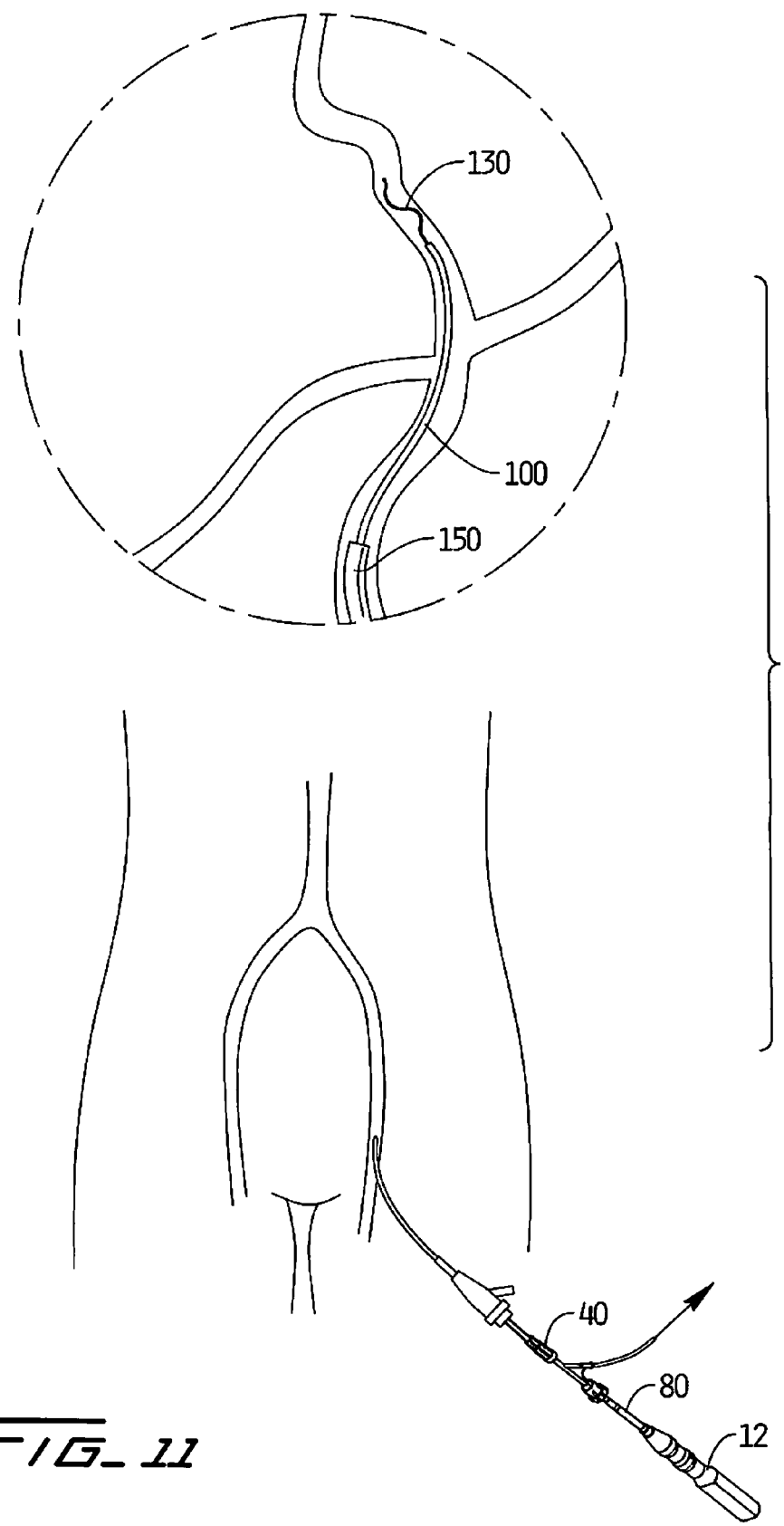
FIG_11

ROTATIONAL THROMBECTOMY WIRE

This application claims priority from provisional application Ser. No. 61/431,169, filed Jan. 10, 2011, and is a continuation in part of Ser. No. 13/095,329, filed Apr. 27, 2011, which claims priority from provisional application Ser. No. 61/334,412, filed May 13, 2010 the entire contents each of these applications are incorporated herein by reference.

BACKGROUND

1. Technical Field

This application relates to a rotational thrombectomy wire for clearing thrombus from native vessels.

2. Background of Related Art

There have been various attempts to break up clots and other obstructing material in grafts or native vessels. One approach is through injection of thrombolytic agents such as urokinase or streptokinase. These agents, however, are expensive, require lengthy hospital procedures and create risks of drug toxicity and bleeding complications as the clots are broken.

Other approaches to breaking up clots involve mechanical thrombectomy devices. For example, U.S. Pat. No. 5,766,191 discloses a cage or basket composed of six memory wires that expand to press against the inner lumen to conform to the size and shape of the lumen. This multiple wire device is expensive and can be traumatic to the graft, possibly causing damage, since as the basket rotates, the graft is contacted multiple times by the spinning wires. Other risks associated with the basket include the possibility of catching onto the graft itself and tearing the graft as well as catching and tearing the suture at the anastomotic site. Additionally, the basket can become filled with a clot which would then require time consuming withdrawal of the basket, cleaning the basket and reinserting it into the lumen. This device could be traumatic if used in the vessel, could denude endothelium, create vessel spasms and has the potential for basket and drive shaft fracture.

U.S. Pat. No. 6,090,118, incorporated herein by reference in its entirety, discloses a wire rotated to create a standing wave to break-up or macerate thrombus. The single wire is less traumatic than the aforedescribed basket device since it minimizes contact with the graft wall while still effectively mechanically removing thrombotic material.

U.S. Pat. No. 7,037,316 discloses another example of a rotational thrombectomy wire for breaking up clots in grafts. The thrombectomy wire has a sinuous shape at its distal end and is contained within a sheath in a substantially straight non-deployed position. When the sheath is retracted, the distal portion of the wire is exposed to enable the wire to return to its non-linear sinuous configuration. The wire is composed of two stainless steel wires wound side by side with an elastomeric tip at the distalmost end. Actuation of the motor causes rotational movement of the wire, creating a wave pattern, to macerate thrombus. Thus, it provides the additional advantages of increased reliability and consistency in creating the wave pattern since the wave pattern created by the standing wave of the '118 patent will depend more on the rotational speed and the stiffness of the wire. Additionally, the sinuous configuration enables creation of a wave pattern at a lower rotational speed.

Although the sinuous wire of the '316 patent is effective in proper clinical use to macerate thrombus in dialysis grafts, it is not best suited for use in native vessels. U.S. Pat. No. 7,819,887, the entire contents of which are incorporated herein by reference, discloses a thrombectomy wire better suited for use in native vessels (and can also be used for deep vein thrombosis and pulmonary embolisms).

In neurovascular thrombectomy procedures, the thrombectomy wire needs to navigate tortuous vessels. That is, the wire is inserted through femoral artery and then must navigate small and tortuous vessels as it is advanced to the smaller cerebral arteries of the brain. Within the brain, the carotid and vertebrobasilar arteries meet to form the circle of Willis. From this circle, other arteries, e.g., the anterior cerebral artery, the middle cerebral artery and the posterior cerebral artery, arise and travel to various parts of the brain. Clots formed in these cerebral arteries can cause stroke and in certain instances death of the patient.

Due to the size and curves of the vessels en route to the cerebral arteries from the femoral artery, as well as the size and structure of cerebral arteries themselves, access is difficult. If the thrombectomy device is too large then navigation through the small vessels, which can be as small as 1 mm, would be difficult. Also, if the device is too stiff, then it can damage the vessel walls during insertion. On the other hand, if the device is too flexible, it will lack sufficient rigidity to be advanced around the vessel curves and can be caught in the vessel. Consequently, it would be advantageous to provide a thrombectomy device for breaking cerebral clots that strikes the optimal balance of flexibility and stiffness, thus effectively having the insertability of a tracking guidewire while enabling high speed rotation to effectively macerate clots without damaging vessels.

SUMMARY

The present invention advantageously provides in one aspect a rotational thrombectomy wire for breaking up vascular thrombus or other obstructive material. The wire comprises a core having a proximal region and a distal region and being rotatable by a motor, the distal region having a smaller diameter than the proximal region. A cable is coupled to the distal region of the core and extends distally thereof. A torque tube is positioned over the cable and a coil is positioned over a distal portion of the cable. The distal portion of the cable has a non-linear configuration. A first covering material is positioned over the coil.

In some embodiments, a hypotube couples a distal end of the core to a proximal end of the cable. A second covering material can cover the torque tube. A heat shrink can cover the first covering material. In some embodiments, the second covering material overlies a portion of the core and extends to a region proximal of the first covering material.

In some embodiments, the non-linear distal region of the cable is sinuous in configuration. In other embodiments, the non-linear distal end of the cable is J-shaped in configuration.

In some embodiments, the wire is removably coupled at a proximal end to a motor drive shaft. The wire can be movable within a lumen of a housing, the housing having a suction port extending therefrom and communicating with the lumen.

In another aspect, the present invention provides an assembly for breaking up vascular thrombus or other obstructive material comprising an introducer sheath having a lumen, a rotational thrombectomy wire slidable within the lumen of the introducer sheath, and a connector having a distal portion connectable to the introducer sheath and a proximal portion connectable to a motor housing, the wire operably connectable to a motor positioned within the motor housing.

The wire can comprise a core having a distal region with a smaller diameter than the proximal region. The wire can further include a cable extending distally of the core, a coil attached to a distal portion of the cable and a first covering material positioned over the coil. In some embodiments, a portion of the cable assumes a non-linear shape when exposed.

A housing having a first lumen can be provided, with the introducer sheath connectable to the housing and insertable through the first lumen. In some embodiments, the housing can include a suction arm having a second lumen, with the second lumen configured to remove particles removed by rotation of the wire. The assembly can further include a catheter extending distally of the housing wherein exposure of the wire from the catheter enables a distal portion of the wire to assume a non-linear configuration. The assembly can further include a motor housing.

In another aspect, the present invention provides a method for removing thrombus in a cerebral artery of a patient comprising the steps of:

introducing a guidewire and a first catheter into the femoral artery;

advancing the first catheter through the vascular system;

removing the guidewire;

providing a housing and a second catheter extending distally from the housing;

providing an introducer sheath;

connecting the introducer sheath to the housing;

inserting a rotational thrombectomy wire through the introducer sheath and through the second catheter;

advancing the thrombectomy wire within the catheter to access the cerebral artery;

subsequently operably coupling a motor to the proximal end of the thrombectomy wire; and activating the motor to rotate the thrombectomy wire to macerate thrombus in the cerebral artery.

In some embodiments, the step of advancing the thrombectomy wire to the cerebral artery includes the step of inserting the thrombectomy wire into the circle of Willis. The method may further include the step of providing a connector tube and attaching a proximal end of the connector tube to a motor housing and a distal end of the connector tube to the introducer sheath. The method may also include the step of providing a vacuum to remove particles from the artery.

BRIEF DESCRIPTION OF THE DRAWINGS

Preferred embodiment(s) of the present disclosure are described herein with reference to the drawings wherein:

FIG. 1 is a perspective view of a first embodiment of a thrombectomy apparatus of the present invention;

FIG. 2 is an exploded view of the proximal portion of the thrombectomy apparatus of FIG. 1;

FIG. 3 is a side view in partial cross-section of the apparatus of FIG. 1 with the rotational wire contained within the introducer sheath;

FIG. 3A is longitudinal cross-sectional view taken along line 3A-3A of FIG. 1;

FIG. 4 is a side view of the apparatus of FIG. 1 showing the rotational wire in a non-linear position corresponding to a position exposed from the introducer sheath;

FIG. 4A is an enlarged view of the distal portion of one embodiment of the thrombectomy wire having a sinuous configuration;

FIG. 4B is an enlarged view of the distal portion of an alternate embodiment of the thrombectomy wire having a J-tip configuration;

FIG. 5 is a longitudinal cross-sectional view of the distal portion of the thrombectomy wire of the apparatus of FIG. 1;

FIG. 8 illustrates insertion of a guide catheter through the femoral artery and into the cerebral artery over a tracking guidewire;

FIG. 9 is a view similar to FIG. 8 illustrating withdrawal of the tracking guidewire;

FIG. 9A is a perspective view illustrating attachment of the RHV to the introducer catheter;

FIG. 10 illustrates insertion of the introducer catheter of the thrombectomy apparatus through a guide catheter and into the circle of Willis and insertion and attachment of the RHV to the introducer catheter;

FIG. 10A is a perspective view illustrating insertion of the introducer sheath into the RHV;

FIG. 10B is a perspective view illustrating attachment of the connector tube to the introducer sheath;

FIG. 10C is a perspective view of another introducer catheter;

FIG. 10D is a side view showing attachment of the RHV and the introducer catheter of FIG. 10C;

FIG. 11 illustrates insertion of the thrombectomy wire of FIG. 1 into the RHV and through the introducer catheter, and continued advancement of the thrombectomy wire of FIG. 1 from the introducer catheter so the distal portion of the wire is positioned in the circle of Willis; and FIG. 12 is a perspective view of an alternate embodiment of the apparatus.

DETAILED DESCRIPTION OF PREFERRED EMBODIMENTS

Figure 7:
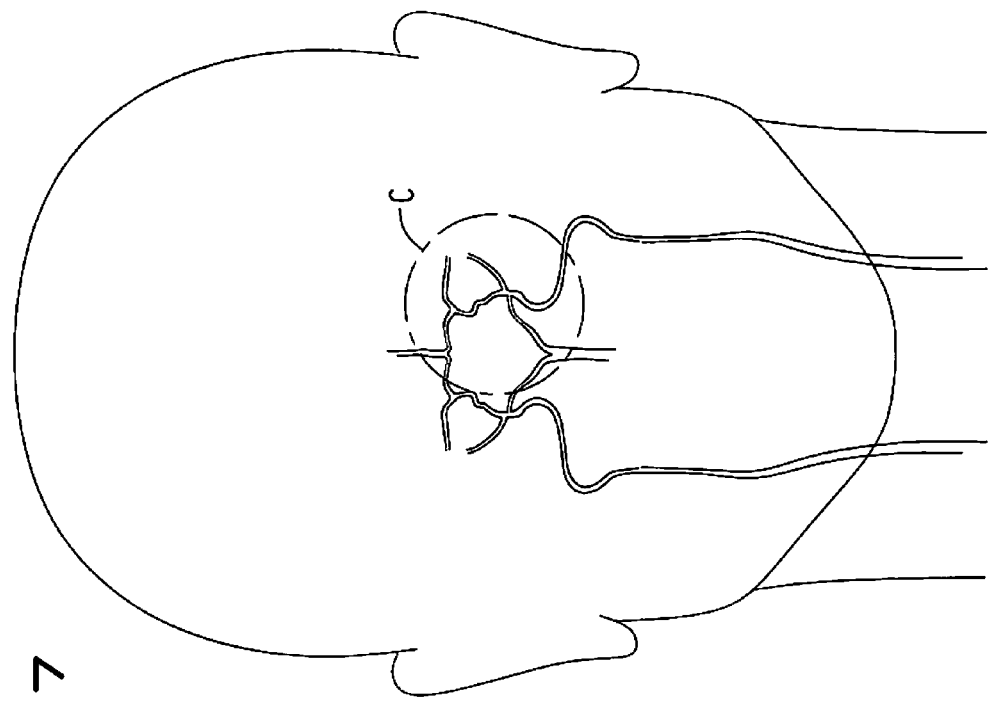
FIG. 7 is a front anatomical view showing select cerebral arteries, including the circle of Willis.

Referring now in detail to the drawings where like reference numerals identify similar or like components throughout the several views, FIG. 1 illustrates a first embodiment of the thrombectomy apparatus of the present invention.

The thrombectomy apparatus of FIG. 1 is designated generally by reference numeral 10. With reference to FIGS. 1 and 2, the apparatus includes a motor housing 12, a rotational thrombectomy wire 30, a rotating hemostatic valve (RHV) 40, an introducer sheath 60 and a telescoping tube or tubular connector 80. The RHV 40 is connectable to an introducer catheter 100 discussed below in conjunction with the method of use (see e.g. FIG. 10). The introducer sheath 60 is insertable into the RHV 40 to facilitate insertion of the thrombectomy wire 30 through the RHV 40 and introducer catheter 100.

The thrombectomy apparatus or assembly 10 disclosed herein provides a rotational thrombectomy wire as a separate unit from a catheter. That is, the thrombectomy wire 30 is provided as a separate unit insertable through the RHV 40. The RHV 40 has a distal end 52 connected to a proximal end of the introducer catheter 100 to access the surgical site. The introducer sheath 60 aids insertion of the thrombectomy wire into the RHV 40 and through the introducer catheter, with the walls of the introducer sheath 60 maintaining the non-linear distal end of the wire 30 in a substantially straightened (substantially linear) configuration as it enters the RHV 40.

Additionally, the thrombectomy wire 30 of the present invention can be slid within the introducer sheath 60 and introducer catheter 100 prior to connection to the motor, if desired. This can aid introduction and manipulation of the wire 30 since it is less cumbersome and of lighter weight than if the motor housing was attached during manipulation of the wire. However, it is also contemplated that the wire 30 could be attached to the motor housing 12 prior to insertion through the introducer sheath 60, RHV 40 and the introducer catheter 100 and thus the wire 30 would be slidable within the introducer sheath 60 (and introducer catheter 100) with the motor housing 12 attached. Thus, the motor housing 12 can be attached to the wire at a desired time prior to or during the procedure.

Turning to the specific components of the thrombectomy apparatus 10, and with reference to FIGS. 1-4, the motor housing 12, which also forms a handle portion, has two identical housing halves 13a, 13b. A motor 14 is seated within recess 14a of housing half 13a and the opposing recess of housing half 13b and has a motor drive shaft 15 extending therefrom. Tabs 15b(FIG. 3) help secure the motor 14 within the housing 12. A gear reducer (not shown) could optionally be provided to reduce by way of example the rotational speed of the motor 14 from 15,000 rpm to 1500 rpm, 750 rpm, 150 rpm, etc. One or more batteries 16, such as a 3 Volt battery, is positioned in recess 17a of housing half 13a and the opposing recess of housing half 13b for powering the motor 14. The battery(s) 16 can be contained within a compartment in the housing 12 accessible by removing a battery door. The motor drive shaft 15 connects to a proximal end of the thrombectomy wire 30 by various couplings, such as for example a snap fit wherein cap 31 at the proximal end of wire 30 is frictionally fit over the motor drive shaft 15. Various other types of connections are also contemplated. A printed circuit board can also be provided within the housing 13 and is designated by reference numeral 18.

Motor housing 12 includes a distal tubular portion 22 having a tab in the form of a ring 24 which fits within a groove in the tube connector 80, best shown in FIG. 3 to connect the motor housing 12 to tube connector 80 described below.

Switch 19 extends though recess 21 in housing half 13a and in a corresponding recess in housing half 13b. A potentiometer (not shown) can optionally be wired to the motor to enable dialing the motor speed up or down to adjust the rotational speed of the thrombectomy wire 30 to adjust for various procedures and/or clot locations and sizes. In a preferred embodiment, the potentiometer is used as a two terminal variable resistor, i.e. a rheostat, by not connecting the third terminal. In this manner, in the initial position, the motor speed is at the desired minimum and rotation of a knob (or in alternate embodiments sliding of a knob) progressively increases the motor speed. Thus, the on/off switch 19 extending from the housing 12 is electrically connected to the motor 14 to turn on the motor 14 to activate the apparatus, i.e. rotate the wire 30.

Turning to the other components illustrated in FIGS. 2-4, rotating hemostatic valve (RHV) or housing 40 is connectable to an introducer catheter 100 (see FIG. 9A). A conventional introducer catheter can be utilized or alternatively a specially designed catheter for use with the apparatus of the present invention. As is standard, the RHV 40 is rotatable with respect to the catheter 100 to alter the orientation of the side arm 56.

Side arm 56 extends from the tubular portion 46 of RHV 40 and has a port 57 for introduction of fluids and/or application of vacuum as described below. Luer lock is provided at the distal end 52 of RHV 40 to connect to the introducer catheter 100 as internal threads 51a of rotation knob 51 threadingly engage external proximal threads of the introducer catheter 100. Tube extension 48 fits within the lumen of the introducer catheter 100 when attached. Washers 49a, 49b help to provide a seal against fluid flow.

Tubular portion 46 of RHV 40 includes a lumen 55 extending therethrough to slidably receive the tubular portion 62 of the introducer sheath 60. Proximal cap 58 at proximal end 54 has internal threads 59 to threadingly attach to external proximal threads 47 of RHV 40 for attachment of the cap 58 to the RHV 40. Further, a crush ring 43 and distal ring 44 are seated within the internal lumen 55 of the tubular portion 46. Thus, as cap 58 is tightened on RHV 40 by rotation, it compresses rings 43 and 44 against the tubular portion 62 of introducer sheath 60 extending therethrough to connect the introducer sheath 60 to the RHV 40. A proximal seal 45 can also be provided. Flange 46a on the proximal end 54 of RHV 40 interacts with lip 58a of cap 58 to allow loosening of cap 58 to release introducer sheath 60 without cap 58 detaching from RHV 40.

Side arm 56 of RHV 40 has a lumen 53 (FIG. 3A) in fluid communication with lumen 55 of tubular portion 46. Fluids such as imaging dye can be injected through the arm 56, flowing through the lumens 53 and 55, i.e. through the space between the inner wall of lumen 55 and the outer wall of the introducer sheath 60, and then through the space between the thrombectomy wire 30 and the inner wall of the introducer catheter 100, exiting a distal opening 103 (FIG. 10) in the introducer catheter 100 to flow into the vessel. This imaging dye can be used to provide an indication that fluid flow has resumed in the vessel.

The side arm 56 can also be used for vacuum to suction particles detached from the vessel by the rotational wire 30. The particles would flow into the distal opening 103 of the introducer catheter 100 and through the space between the wire 30 and the inner wall of the introducer catheter 100, continuing through lumen 55 and then exiting through lumen 53 and port 57 into a suction tube (not shown).

It should also be appreciated that the guide catheter 150 discussed in conjunction with the method of use below can also have a side arm for injection of fluid (see e.g. side arm 152 of FIG. 8).

In the alternate embodiment of FIG. 12, the RHV ' does not have a side arm. In this embodiment, a guide catheter with a side arm can be used for injection and suction. Otherwise the components are identical to the components of FIG. 1 and for convenience, the corresponding components are labeled with "prime" designations e.g., rotational knob 51', cap 58', introducer sheath 60', connector tube 80' and locking cap 83'.

The tubular portion 62 of introducer sheath 60, as noted above, extends through the lumen 55 of RHV 40 and terminates either within RHV 40 or at a proximal portion of the lumen of the introducer catheter 100. The tubular portion 62 preferably has a stiffness greater than the stiffness of the thrombectomy wire 30 to maintain the wire 30 in a straightened position during passage of wire 30 into the RHV 40 for subsequent passage through the lumen of the introducer catheter 100 to the surgical site.

Proximal end 65 of introducer sheath 60 is attachable to connector tube 80. Preferably, the enlarged proximal end 65 has a threaded flange 67 as shown in FIG. 3A to threadingly engage the internal threads 85 on the distal cylindrical locking cap 83 at the distal end 82 of tubular connector 80. A valve can be provided within the distal end 82 of the connector tube 80 in addition or instead of a valve in a proximal end 65 of the introducer sheath 60 to seal escape of fluid to improve the vacuum through the side arm 56.

Note the tube 80 and introducer sheath 60 can alternatively be provided as one unit, attached together and positioned over the thrombectomy wire 30 as an attached unit. However, in alternative embodiments, the wire 30 is inserted through the introducer sheath 60 and manipulated through the introducer catheter 100 to the surgical site. Once positioned, the connector tube 80 is then threadingly attached at the distal end 82 to the introducer sheath 60 as noted above and at a proximal end 84 to the motor housing 12. In this version, the connector tube 80 can be positioned over the wire 30 prior to insertion of the wire 30 through introducer sheath 60 or after insertion through the sheath 60. The wire 30 can be packaged with the sheath 60 and the tube 80 positioned thereover, or packaged apart from the sheath 60 and tube 80.

Proximal end 84 of connector tube 80 is configured for attachment to the motor housing 12 by an external ring 24 on tip 22 of motor housing 12. Ring 24 is seated within an internal groove of connector tube 80, as shown in FIG. 3, to provide a snap fit. Other types of attachment are also contemplated. The proximal end of the wire 30 is attached to the drive shaft 15 of the motor 14. In one embodiment, end cap 31 of wire 30 is snap fit within opening 15a in motor shaft 15. Other ways to attach the wire 30 and motor shaft 15 are also contemplated such as a bayonet mount for example.

As can be appreciated, by having a detachable motor housing 12, different handles with different motor speeds and/or different batteries can be utilized by attachment to the wire 30. This can even be achieved during the same surgical procedure.

In some embodiments, the housing can be detached, sterilized and reused after recharging of the battery or replacing the battery.

In some embodiments, as an alternative to direct connection to the motor shaft, the proximal end of wire 30, after insertion to the surgical site or prior to insertion, can be attached at a proximal end to a coupler tube which is connected to a gear reducer. The connection can be a friction fit, a magnetic coupling or a twist connect, e.g. a bayonet connection, by way of example.

FIG. 5 illustrates one embodiment of the thrombectomy wire 30 of the present invention. The wire 30 has a distal coiled tip 91. In preferred embodiments, the distal coiled tip (and underlying cable) is angled with respect to the longitudinal axis. FIG. 4A shows the wire of FIG. 5 forming a sinuous shape. In FIG. 4B, an alternative embodiment of the wire is illustrated, wherein the wire 130 forms a J-tip which creates a standing wave upon rotation. In the J-tip configuration, due to the angle, when the wire is rotated by the motor at sufficient speed at least one vibrational node is formed. Details of this creation of a standing wave are described in U.S. Pat. No. 6,090,118, the entire contents of which are incorporated herein by reference.

In the embodiment of FIG. 4A, the wire 30 forms a substantially sinuous shape, resembling a sine curve. More specifically, wire 30 of FIG. 4A has a substantially linear portion extending through most of its length, from a proximal region, through an intermediate region, to distal region 36. At the distal region 36, wire 30 has a sinuous shape in that as shown it has a first arcuate region 33 facing a first direction (upwardly as viewed in the orientation of FIG. 4A) and a second arcuate region 35, spaced longitudinally from the first arcuate region 33, facing a second opposite direction (downwardly as viewed in the orientation of FIG. 4A). These arcuate regions 33, 35 form "peaks" to contact vascular structure as the wire 30 rotates. This angled (non-linear) distal portion of wire 30 includes a coiled portion with a covering material to block the interstices of the coil as discussed in more detail below. Note in a preferred embodiment, the amplitude of the proximal wave (at region 33) is smaller than the amplitude of the distal wave (at region 35), facilitating movement in and out of the catheter.

When the wire 30 is fully retracted within the introducer catheter 100 (as in FIG. 3), the curved regions of the wire 30 are compressed so the distal region 36 is contained in a substantially straight or substantially linear non-deployed configuration. When the introducer catheter 100 (attached to RHV 40) is retracted by proximal axial movement (see the arrow of FIG. 4), or the wire 30 is advanced with respect to the introducer catheter 100, or the wire 30 and catheter 100 are both moved in the respective distal and proximal directions, the distal region 36 of the wire 30 is exposed to enable the wire 30 to return to its non-linear substantially sinuous configuration shown in FIG. 4A (and FIG. 4) for rotation about its longitudinal axis within the lumen of the vessel.

Thus, as can be appreciated, the wire 30 is advanced within the introducer catheter 100 which is attached at its proximal end to the distal end of the RHV 40. When at the desired site, the wire 30 and introducer catheter 100 are relatively moved to expose the wire 30 to assume its non-linear shape for motorized rotational movement to break up thrombotic material on the vessel wall. If a J-tip wire, such as wire 130 of FIG. 4B, is utilized, the wire 130 can be rotated within the introducer catheter 100 to re-orient the wire 130.

The flexible tubular portion 62 of the introducer sheath 60 can optionally contain one or more braided wires embedded in the wall to increase the stiffness. Such braided wires would preferably extend the length of the sheath 60.

In an embodiment of the coiled tip being composed of shape memory material, the memorized configuration is sinuous or s-shape as in FIG. 4A. In the state within the introducer catheter 100, the wire is in a substantially linear configuration. This state is used for delivering the wire to the surgical site. When the wire is exposed to warmer body temperature, the tip transforms to its austenitic state, assuming the s-shaped memorized configuration. Alternatively, the coiled tip of the wire can be compressed within the wall of the introducer catheter and when released, assumes its shape memorized non-linear shape. The coiled tip can alternatively be a radiopaque coil/polymer pre-shaped to an "S".

Details of the wire 30 will now be described with reference to FIG. 5. These details are the same for wire 130, the only difference being that instead of the distal coiled tip of the wire being sinuous shaped in the deployed position, the distal tip of the wire is in a J-configuration. Note it is also contemplated that in an alternate embodiment the distal tip of the wire can be substantially straight (substantially linear) in both the covered and deployed (exposed) position. For convenience, details will be discussed with reference to wire 30.

Wire 30 has a core 32 having a proximal portion 34 (see FIG. 2) and a distal portion 37 (FIG. 5). Transition region 38 of core 32 is tapered distally so that the diameter of the distal portion 37 of core 32 is less than the diameter of the proximal portion 34. A uniform diameter portion 37a extends distal of tapered portion 37. The taper in transition region 38 can be formed by removing a coating, such as a PTFE coating, placed over the core 32 and a grinding of the core 32. In one embodiment, the core 32 is a solid material made of a nickel titanium alloy, although other materials are also contemplated. The core 32 can also be formed from a hypotube with a tapered body attached, e.g. welded, to the distal end of the hypotube.

The core 32 is connected to a cable 90. The cable 90 can be formed of a plurality of wires twisted together such as a 1×19 wire for example. The twisted wires can be surrounded by additional wires or a sheath. The core 32 is tapered to accommodate connection to cable 90. Hypotube 92 is placed over the distalmost end of the core 32 (the uniform diameter portion 37a) and the proximalmost end of the cable 90 and is attached thereto by a number of methods, including but not limited to, laser welding, soldering or crimping. The hypotube 92 thereby forms a coupler for joining the core 32 and cable 90 as these components are positioned within the hypotube 92. The hypotube can have a diameter of about 0.010 inches, although other dimensions are contemplated.

The cable 90 in one embodiment has a variable stiffness such that the proximal portion 94 is stiffer, e.g. has a tighter braid, than a distal portion 96 to increase the flexibility of the distal portion 96. In other embodiments, the cable 90 is of uniform stiffness. The cable 90 can be of substantially uniform diameter. Various covering materials, e.g. coating, jackets and/or shrink wraps, can be used as an alternative or in addition to vary the stiffness of the cable 90.

A torque tube 97 is positioned over the cable 90. The torque tube 97 extends distally from a tapered region of the core 32, terminating at the distal coil 91. The torque tube 97 can be soldered at (proximal) end 97a to the core 32 and at a distal region 97b (e.g. at a distal end) to the cable 90. The torque tube 97 can also be attached, e.g. soldered or laser welded, to a proximal end of the coil.

A polymer coating(s) and/or jacket(s) can be placed over the torque tube 97 to cover the interstices in the cable 90 and provide a smooth surface. In one embodiment, a PTFE shrink wrap tubing 98 is placed over the torque tube 97 and over a portion of the core 32, preferably extending over the tapered transition region 38 of core 32 to terminate at a proximal end adjacent the uniform diameter region of the core 32. At a distal end, the shrink wrap 98 terminates at the end where the torque tube 97 terminates.

Coiled tip 91 is positioned over a distal portion of the cable 90, and preferably over the distal tip. The coil 91 in one embodiment is composed of a soft and malleable material such as platinum and has a uniform pitch and diameter. The distalmost tip of the cable 90 can have a laser welded ball to which the coil 91 is welded to enhance retention of the coil 91 and cable 90. The coiled tip region has a substantially sinuous configuration. In an alternate embodiment, the coiled tip region has a J-tip configuration, as shown for example in FIG. 4B. The coiled tip region can alternatively have a substantially linear configuration in the deployed/uncovered position. In each of these embodiments, preferably a covering such as a jacket, shrink wrap or coating covers the coil 91. In a preferred embodiment, a nylon covering 99 is heat fused over the coil 91, to melt into the interstices. A heat shrink tubing 99a, such as FEP, in some embodiments, is placed over the heat fused nylon coating. The covering 99, and heat shrink tubing 99a, terminate adjacent a distal end of the torque tube 97 and adjacent a distal end of the shrink wrap 98.

By way of example only, the components of wire 30 can have the approximate dimensions set forth in the table below. It should be understood that these dimensions are being provided by way of example as other dimensions are also contemplated. These are also approximate values.

| COMPONENT | APPROXIMATE OUTER DIAMETER | APPROXIMATE LENGTH |
|---|---|---|
| Core 32 (proximal non tapered portion) | .016 inches | 139.5 cm |
| Core tapered portion | .016 inches to .0095 inches | 4.35 inches |
| Distal coil 91 | .016 inches | 3.0 inches |
| Torque tube 97 | .013 inches | 8.0 inches |
| Shrink tube 98 | .014 inches | 10.35 inches |
| Cable 90 | .010 inches | 8.2 inches |

The covering material, e.g. coating, jackets, and or shrink wraps, helps to prevent bending or knotting of the wire which could otherwise occur in native vessels. The covering also increases the torsional strength of the wire and also strengthens the wire to accommodate spasms occurring in the vessel. The coating also blocks the interstices of the coil 91 to provide a less abrasive surface. The various coating and/or jackets and/or shrink wrap can be made of PET, Teflon, Pebax, polyurethane or other polymeric materials. The material helps to prevent the native vessel from being caught in the coil 90 and reduces vessel spasms.

The use of the thrombectomy apparatus 10 will now be described. The use, by way of example is shown and described with respect to the embodiment of FIG. 1 with the sinuous tip wire of FIG. 4, it being understood that the wire embodiment of FIG. 4B would be utilized in a similar manner.

Figure 6:
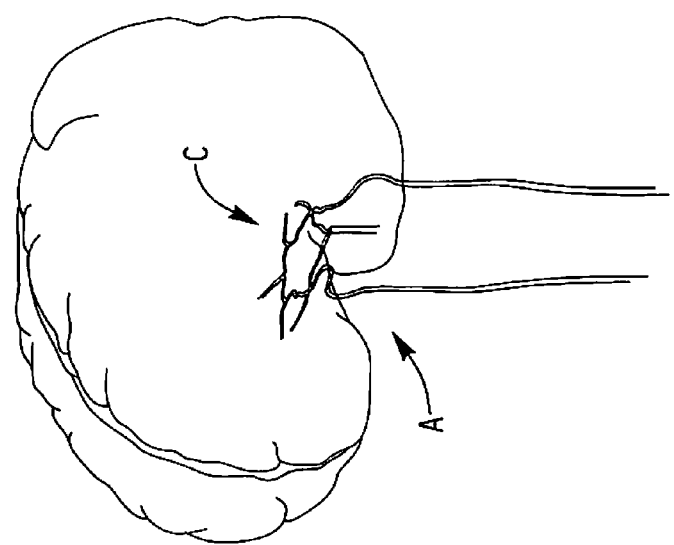
FIG. 6 is an anatomical view showing select cerebral arteries.

An access sheath (not shown) is inserted into the vessel and then a guidewire e.g. 0.035 or 0.038 inches in diameter, and a guide catheter 150 are inserted through the sheath and advanced through the vasculature. The guidewire is removed and a smaller diameter guidewire G, e.g. 0.014 inch diameter, and the introducer catheter 100 are inserted through the guide catheter 150 and access sheath with the guidewire G in the femoral artery F and located via imaging. The introducer catheter 100 is advanced to the desired site through the vascular system into the cerebral arteries A, for example through the Circle of Willis C (see FIGS. 6, 7 and 8). Once at the site, the guidewire G is withdrawn as shown in FIG. 9. Note the introducer catheter 100 is preferably inserted with the RHV 40 attached. That is, the tubular portion 46 of the RHV 40 is inserted through the introducer catheter 100 (see FIG. 10) and attached thereto by rotation of cap 51 as shown in FIG. 9A. In the alternate embodiment of FIGS. 10C and 10D, RHV 40 is attached to thread 124 of the winged luer fitting of introducer catheter 120 by rotation of cap 51 and/or winged handle 122.

Note in an alternate embodiment, instead of the RHV 40 attached prior to introduction of the introducer catheter 100 through the guide catheter 150, it can be attached after introduction of catheter 100 through guide catheter 150.

The introducer sheath 60 is inserted through the RHV 40, and attached to the RHV 40 by rotation of cap 58 as shown in FIG. 10A. The thrombectomy wire 30 is inserted through the lumen of the introducer sheath 60, through the lumen of the RHV 40 and into the lumen of the introducer catheter 100. The introducer catheter 100 extends from the guide catheter 150 as shown in FIG. 10, but the wire 30 remains inside the introducer catheter 100. The distal end of the wire 30 is then exposed from the introducer catheter 100 at the target surgical site by relative movement of the wire 30 and introducer sheath 100. Note the wire 30 can be attached to the motor drive shaft 15 at this point or can be attached before exposed or at any other time in the procedure such as prior to insertion of the wire 30 through the introducer sheath 60. Attachment is achieved by connection of the connector tube 80 to the introducer sheath 60 (see FIG. 10B) and attachment of the proximal end of the connector 80 to the motor housing 12. The wire 30 extends through the connector tube and attachment of the wire 30 (which extends through connector 80) to the motor drive shaft 15. As noted above, alternatively, the connector tube 80 can be connected to the introducer sheath 60 prior to attachment to the motor housing 12, or alternatively connected after the wire 30 is at the surgical site and exposed from the introducer sheath.

With the wire 30 exposed from the introducer catheter 100, switch 19 on housing 12 is actuated to turn on the motor 14 thereby causing wire 30 to rotate about its longitudinal axis to break up/macerate thrombus.

The macerated particles can be removed by suction through side arm 56 of RHV 40 as the particles travel in the space between wire 30 and introducer catheter 100 and RHV 40. The introducer catheter 100 can optionally have a side port(s) and/or the guide catheter 150 can optionally have a side port(s) such as side port 152 for aspirating the small macerated particles in addition to or alternative to side arm 56 of RHV 40.

The delivery (access) sheath or delivery catheter 100 can include a balloon (not shown) to block blood flow and allow aspiration in the blocked space.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A rotational thrombectomy wire for breaking up vascular thrombus or other obstructive material, the thrombectomy wire comprising a core having a proximal region and a distal region and being rotatable by a motor, the distal region having a smaller diameter than the proximal region, a cable coupled to the distal region of the core and extending distally thereof, a torque tube positioned over the cable, a coil positioned over a distal portion of the cable, the distal portion of the cable has a non-linear configuration, and a first covering material positioned over the coil, wherein a second covering material covers the torque tube.

2. The thrombectomy wire of claim 1, further comprising a heat shrink material covering the first covering material.

3. The thrombectomy wire of claim 1, wherein the non-linear distal portion of the cable is sinuous in configuration.

4. A rotational thrombectomy wire for breaking up vascular thrombus or other obstructive material, the thrombectomy wire comprising a core having a proximal region and a distal region and being rotatable by a motor, the distal region having a smaller diameter than the proximal region, a cable coupled to the distal region of the core and extending distally thereof, a torque tube positioned over the cable, a coil positioned over a distal portion of the cable, the distal portion of the cable has a non-linear configuration, and a first covering material positioned over the coil, and a second covering material overlying a portion of the core and extending over the torque tube to a region proximal of the first covering material.

5. The thrombectomy wire of claim 4, wherein the non-linear distal portion of the cable is sinuous in configuration.

6. An assembly for breaking up vascular thrombus or other obstructive material, the assembly comprising:
    an introducer sheath having a lumen;
    a rotational thrombectomy wire slidable within the lumen of the introducer sheath; and
    a connector having a distal portion and a proximal portion, the distal portion connectable to the introducer sheath and the proximal portion connectable to a motor housing, the wire selectively operably connectable by a user at a desired time for a procedure to a motor positioned within the motor housing.

7. The assembly of claim 6, wherein the wire comprises a core having a proximal region and a distal region, the distal region having a smaller diameter than the proximal region, and the wire further includes a cable extending distally of the core, a coil attached to a distal portion of the cable and a first covering material positioned over the coil.

8. The assembly of claim 7, wherein the distal portion of the cable and the coil assume a non-linear configuration when exposed from a catheter.

9. The assembly of claim 6, further comprising a housing having a first lumen, the introducer sheath connectable to the housing, and insertable through the first lumen.

10. The assembly of claim 9, wherein the housing includes a suction arm having a second lumen, and the second lumen configured to remove particles removed by rotation of the wire.

11. The assembly of claim 9, further comprising a catheter extending distally of the housing, wherein exposure of the wire from the catheter enables a distal portion of the wire to assume a non-linear configuration.

* * * * *